United States Patent [19]

Elgebaly

[11] Patent Number: 5,318,891
[45] Date of Patent: Jun. 7, 1994

[54] DIAGNOSTIC TEST PROCEDURE FOR URINARY TRACT INFLAMMATORY CONDITION

[75] Inventor: Salwa A. Elgebaly, Bloomfield, Conn.

[73] Assignee: The University of Connecticut, Farmington, Conn.

[21] Appl. No.: 912,072

[22] Filed: Jul. 8, 1992

Related U.S. Application Data

[63] Continuation of Ser. No. 521,522, May 10, 1990, abandoned.

[51] Int. Cl.$^5$ .............................................. G01N 33/53
[52] U.S. Cl. ..................................... 435/7.24; 436/63; 436/811; 435/29
[58] Field of Search .................... 435/7.24, 7.92, 29; 436/811, 63

[56] References Cited

PUBLICATIONS

Elgebaly et al., Urinary Neutrophil Chemotactio Factors in Interstitial Cystitis Patients and a Rabbit Model of Bladder Inflammation, The Journal of Urology 147:1382-1387, 1992.

Robbins, S. L., Pathologic Basis of Disease, W. B. Saunders Co., Philadelphia, 1974. pp. 1156-1159.

Henry, J. B., Clinical Diagnosis and Management by Laboratory Methods, W. B. Saunders Co., Philadelphia, 1979. pp. 1343-1347.

Primary Examiner—Esther L. Kepplinger
Assistant Examiner—Donna C. Wortman
Attorney, Agent, or Firm—Chilton, Alix & Van Kirk

[57] ABSTRACT

The invention provides a diagnostic test procedure for detecting the active status of interstitial cystitis, a chronic inflammatory disease of the bladder. Determination of chemotactic activity present in fluid that has been exposed to urinary tract tissue is performed by measuring cell migration across a membrane in response to neutrophil chemotactic factors in the fluid.

6 Claims, No Drawings

DIAGNOSTIC TEST PROCEDURE FOR URINARY TRACT INFLAMMATORY CONDITION

This is a continuation of copending application Ser. No. 07/521,522 filed on May 10, 1990, now abandoned.

BACKGROUND AND SUMMARY OF THE INVENTION present invention relates to a diagnostic test procedure for detecting the active status of a noninfectious inflammatory condition such as interstitial cystitis.

Interstitial cystitis (IC) is a chronic debilitating inflammatory disorder of the bladder. The disease is most common in women ranging in age from about thirty to sixty with onset of the condition typically occurring at about forty years of age. The most prevalent symptoms include severe abdominal pain and urinary urgency two or three times per hour, day and night. The initiating causes are unknown and there is no known cure although alleviation of the symptoms can be obtained from selected treatment such as the use of dimethyl sulfoxide (DMSO). The condition is categorized as "interstitial cystitis" because it is believed the disease does not affect the surface of the bladder but instead involves the spaces between the cells, namely the interstices, in the lining of the bladder. Studies have indicated interstitial cystitis is not an auto-immune disease and no evidence exists that it is caused by infectious agents such as aerobic or anaerobic bacteria, viruses and the like. Accordingly, diagnosis is very difficult and treatments have met with limited success.

It has been found that even a cystoscopic examination, which is the insertion of a long thin viewing instrument into the bladder, will not lead with certainty to a diagnosis. Diagnosis using biochemical and laboratory test also have not proved to be extremely helpful. A urine culture can be taken to determine if a bacterial infection is present and thereby rule out other diseases. If no infection or disease is found, a hydrodistentive cystoscopic examination can be carried out under anesthesia. In this procedure the bladder is stretched by filling it with irrigating fluid and the bladder wall is carefully examined cystoscopically. This is the only known way of detecting the characteristic mucosal abnormalities associated with interstitial cystitis, namely the tiny hemorrhages and scar tissue on the bladder wall. Since diagnosis can be uncertain even when using this highly invasive hydrodistention technique, other factors such as case history, urine analysis and culture, bladder biopsy and response to therapy all must also be taken into consideration for a proper diagnosis.

In accordance with the present invention, it has been found that noninfectious inflammatory disorders, such as interstitial cystitis, can be diagnosed in a far less invasive manner with a high degree of accuracy through the utilization of the diagnostic procedure of the present invention. More specifically, this diagnostic procedure is capable of detecting the active inflammatory status of the tissue, including that caused by interstitial cystitis and other inflammatory disorders, through the simple detection of an inflammatory marker in fluid exposed to the inflamed tissue. Advantageously, the procedure will provide not only positive results during inflammation but also a negative test result when the condition is in remission, thereby adding to the specificity of the diagnostic procedure. It will, accordingly, be understood that the diagnostic procedure results in an indication of an active inflammatory condition rather than a determination of the presence in its passive state or absence of a particular disorder.

These and related advantages are achieved in accordance with the present invention by assaying fluids that have been in contact with the inflamed tissue, such as urine samples, or where necessary, by assaying urinary bladder biopsy specimens for the presence or absence of inflammatory mediators such as neutrophil chemotactic factors that stimulate the migration of neutrophils into sites of tissue damage.

In accordance with the present invention, it is believed that the inflammatory condition, such as occurs in interstitial cystitis, is accompanied by the release of inflammatory mediators that attract neutrophils. These neutrophil chemoattractants differ in their biochemical characteristics and molecular weight from previously known low molecular weight factors such as immune cell derived interleukin-1 or leukotriene $B_4$. In accordance with the present invention, it has been found that neutrophil chemotactic factors (NCFs) are present in fluids exposed to the inner wall of the urinary bladder, such as urine, and by assaying the urine sample for the presence of neutrophil chemotactic factors it is possible to determine whether an active state of inflammation exists. The presence of the neutrophil chemotactic factors permits the isolation of antibodies specific for those chemotactic factors. Neutrophil chemotactic factors found in a variety of tissues and in various species are tissue specific and capable of signalling the initial inflammatory condition of the tissue to stimulate neutrophil migration to the inflamed area. Thus, the identification of the presence of the neutrophil chemotactic factors in the urine sample or bladder biopsy specimen provides a positive indication of the condition and a non-invasive diagnostic technique for detecting an active interstitial cystitis condition.

DESCRIPTION OF A PREFERRED EMBODIMENT

Although studies have shown that neutrophils appear in reperfused myocardium following cardiac bypass surgery and in experimentally induced coronary occlusion followed by reperfusion, the presence of chemical signals or mediators has not been reported for disorders such as interstitial cystitis. In accordance with the present invention, it has been found that the tissue of the urinary tract releases neutrophil chemoattractants. The presence of bladder-derived inflammatory mediators in the urine samples of patients with interstitial cystitis suggests the role of the neutrophil chemotactic factors in such bladder disorders. Assays for NCFs may be used in detecting subclinical inflammation and determining the progress and/or remission of the disease. Thus, the presence or absence of the factors can be used as markers for the active/passive status of the interstitial cystitis disease.

The identification of these chemotactic factors also facilitates the development of nonsteroidal anti-inflammatory drugs to effectively treat interstitial cystitis patients. The development of these drugs will have the advantage of controlling urinary bladder inflammation without subjecting the patients to immunosuppression. In addition, the biochemical characterization of the factors will permit the development of enzyme-linked immune-specific assays (ELISAs) for interstitial cystitis.

The chemotactic activity associated with an active IC condition can be measured using methods known in the art. Conveniently such measurements may be made using a modified Boyden's chamber. The standard tripeptide f-Met-Leu-Phe (f-MLP) is used as the positive control for 100% chemotactic response while Hank's balanced salt solution (HBSS) is used as the negative control for random migration. The response to the putative chemoattractants is expressed as percent maximum chemotactic response induced by f-MLP.

A suitable procedure for measuring the chemotactic activity is that described by Elgebaly et al. in the Journal of Molecular Cell Cardiology, Vol. 21, pp. 585–593 (1989) and in the American Journal of Pathology, Vol. 126, pp. 40–50 (1987), incorporated herein by reference. Urine samples obtained from patients are refrigerated and preferably assayed on the same day for neutrophil chemotactic activity. These samples may be filtered or centrifuged prior to testing but generally this is not necessary and the samples are tested in an as-received condition.

A small sample of the material to be tested is placed in the bottom compartment of a Boyden's chamber containing a micropore membrane of controlled characteristics, such as a Millipore membrane having a thickness of 100 microns and a porosity of from 5 microns to 8 microns. The chamber is then incubated for one hour at 37° C. to permit cell migration across the membrane. Following incubation, the filter is removed, fixed with ethanol, stained using hematoxylin and mounted on glass slides for counting cell migration using an Optomax image analyzer. Triplicate filters are used for each test and three readings are taken at random for each filter. Cell migration response to the chemoattractants is measured as the chemotactic index (distance traveled in the filter times the number of cells) and is expressed as percent maximum chemotactic response induced by f-MLP according to the formula set forth in the above mentioned publications.

Chemotactic activity also may be assayed using conventional monoclonal or polyclonal antibody immunoassays, such as radio immune assay (RIA) or enzyme-linked immune specific assays (ELISA). The bladder-derived neutrophil chemotactic factors may be purified, concentrated and used to develop the antibodies, such as by injection of homogenized factor fractions into rabbits over a period of time, for example, about two to four weeks. Polyclonal antibodies for the factors are isolated from the serum of the immunized rabbits with specificity determined by immunoelectrophoresis against the purified neutrophil chemotactic factors. Alternatively, monoclonal antibodies can be made using conventional techniques well known in the art (for example, see Diamond et al, Monoclonal Antibodies: A New Technique for Producing Serological Reagents, New Eng. J. Med. 304:1344, 1981). The antibodies are then used in a multi step enzyme-linked immune specific assay (ELISA) conducted in a conventional manner well known to those skilled in the art in order to provide a diagnostic marker for an active IC condition. The ELISA system for the NCF can also be used to quantitatively detect low levels of the NCF. In turn, specific blockers can be developed to regulate the accumulation of inflammatory cells in the bladder to regulate and control the disease.

In accordance with the present invention, it has been found that significant chemotactic activity will result in maximum response levels well above 15% of the standard f-MLP with substantially all positive readings having a maximum response level of at least 50% or greater. Chemotactic activity found in urinary bladder specimens obtained from the interstitial cystitis patients has been found to be stable for weeks in collected samples held at refrigerated temperatures. It is significant that samples collected from interstitial cystitis patients do not contain leukotriene-$B_4$ or interleukin-1.

The effectiveness of the diagnostic procedure has been measured using diagnosed interstitial cystitis patients, normal healthy volunteers and interstitial cystitis patients treated with DMSO as well as non-interstitial cystitis patients with previous bladder conditions. When urine samples both from patients diagnosed as having interstitial cystitis and from age matched normal volunteers were tested for neutrophil chemotaxis in accordance with the present invention, high levels of chemotactic activity, that is, chemotactic response levels of about 85% of the standard, were found in urine samples of the interstitial cystitis patients while no activity at all was noted in urine samples obtained from the normal volunteers. It was also found that chemotactic activity was absent in urine samples obtained from interstitial cystitis patients that had been treated with DMSO for the previous four to six years. Since DMSO does not suppress the neutrophil migration, the observed reduction in activity is not due to a direct inhibitory effect induced by DMSO. Other patients tested shortly before and shortly after treatment with DMSO showed high chemotactic activity before DMSO treatment and no chemotactic activity after treatment. Urine samples from controlled non-interstitial cystitis patients who exhibited lower urinary tract conditions were evaluated for levels of chemotactic factor. No chemotactic activity was recovered in samples obtained from patients with previous bladder tumor, bladder cancer or benign prostate hyperplasia. Chemotactic activity also was not detected in urine samples obtained from patients with bacterial infection or pelvic pain.

The following specific examples are given in order that the present invention may be more fully understood. These examples are set forth for the purpose of illustration only and are not intended in any way to limit the practice of the invention. Unless otherwise specified, all parts are given by weight.

EXAMPLE I

Urine samples were taken from six female patients ranging in age from 35 to 60 years and previously diagnosed as having interstitial cystitis. Urine samples were also taken from six age-matched normally healthy female volunteers. The urine samples from all participants were refrigerated and assayed on the same day for chemotactic activity using the modified Boyden's chamber. The indicator cells were rabbit peritoneal neutrophils obtained from the peritoneal cavity of white New Zealand rabbits four hours after intraperitoneal injection of 300 milliliters of 0.15M sodium chloride containing 0.1% oyster glycogen. The rabbit neutrophils were adjusted to a final density of $2.5 \times 10^6$ cells per milliliter in Hank's balanced salt solution (HBSS) (the negative control for random migration) containing 0.1% bovine serum albumin (BSA). A 150 ul specimen of the neutrophil suspension was placed in the upper compartment of the modified Boyden's chamber containing a 100 microns thick micropore membrane of porosity 8 microns. The lower compartment of the chamber was charged with 140 ul of the urine samples, f-MLP or HBSS. The chambers were then incubated for one hour at 37° to permit cell migration across the membrane.

Following incubation, the filters were removed, fixed with 100% ethanol, stained with 100% hematoxylin and mounted on glass slides for counting the number cells and distance traveled, using an Optomax image analyzer. All measurements were made in triplicate and migrated cells were counted in six different areas within the two filters using a high power (40x) field. Cell migration in response to the putative chemoattractants are expressed as percent maximum chemotactic response (percent MCR) of f-MLP. This is derived from the calculation of relative chemotactic indices mentioned hereinbefore. The chemotactic index (CI) is defined as the product of the cell number and the distance traveled in the filter. All data is expressed as a mean value and Student's unpaired t-test is used for statistical analysis.

Average chemotactic activity levels of 85% plus or minus 9% were recovered in urine samples from the six interstitial cystitis patients. No activity was recovered in urine samples obtained from the age-matched normal healthy volunteers.

EXAMPLE II

Urine samples from four patients previously diagnosed with interstitial cystitis were tested using the procedure of Example I. Average chemotactic activity levels of 92% were obtained for these samples.

EXAMPLE III

The procedure of Example I was repeated using urine samples obtained from four interstitial cystitis patients treated with dimethyl sulfoxide for the past four to six years. No chemotactic activity was found in the urine samples of these patients.

EXAMPLE IV

A urinary bladder biopsy specimen was obtained from a patient diagnosed as having interstitial cystitis. The specimen was placed in a sterile container containing ten milliliters of sterile saline. Chemotactic activity (50%–55% of f-MLP) in the supernatant solutions was stable for seven days at 4° C.

EXAMPLE V

Urine samples from three interstitial cystitis patients before and after dimethyl sulfoxide treatment were evaluated using the procedure of Example I. Although high levels of chemotactic activity were recovered in urine samples one week before dimethyl sulfoxide treatment, the activity was absent and resulted in a 0% reading one week after treatment. For the second and third patients, activity remained undetected in urine samples collected weekly for five consecutive weeks. The specific results are as set forth in the following table:

| Patient No. | Chemotactic Activity (% f-MLP) | |
| --- | --- | --- |
| | Before DMSO | After DMSO |
| 1 | 66% | 0% |
| 2 | 172% | 0% |
| 3 | 168% | 0% |

EXAMPLE VI

Urine samples from more than a dozen non-interstitial cystitis patients having the various lower urinary tract conditions mentioned below were evaluated for levels of neutrophil chemotactic factor using the procedure of Example I. No chemotactic activity was recovered in urine samples obtained from patients with previous bladder tumor, bladder cancer, bacterial infection, benign prostate hyperplasia or pelvic pain, thus indicating an absence of neutrophil chemotactic factor in urine samples from patients with lower urinary tract conditions other than interstitial cystitis.

As will be apparent to persons skilled in the art, various modifications, adaptations and variations of the foregoing specific disclosure can be made without departing from the teachings of the present invention.

What is claimed is:

1. A diagnostic test procedure for detecting the active status of interstitial cystitis comprising the steps of providing a fluid that has been exposed to tissue of the urinary tract, said fluid selected from the group consisting of urine and supernatant solution exposed to a urinary tract tissue biopsy, and conducting an assay to determine chemotactic activity in said fluid by measuring cell migration across a membrane in response to the presence of neutrophil chemotactic factors in said fluid and determining the level of chemotactic activity of said fluid relative to a standard reagent expressed as a percentage of chemotactic response, a level greater than 15 percent of that obtained using the standard reagent being indicative of the active status of interstitial cystitis.

2. The diagnostic test procedure of claim 1 wherein the presence of chemotactic factors is calculated as a percent maximum chemotactic response relative to positive and negative chemotactic controls.

3. The diagnostic test procedure of claim 1 wherein the standard reagent is f-Met-Leu-Phe.

4. The diagnostic test procedure of claim 1 including the step of using the tripeptide f-Met-Leu-Phe during the assay as a positive standard and wherein the percent maximum chemotactic response to said fluid is at least 50 percent.

5. The diagnostic test procedure of claim 1 wherein the fluid exposed to the tissue is urine.

6. The diagnostic test procedure of claim 1 wherein the fluid exposed to the tissue is the supernatant solution exposed to a tissue biopsy.

* * * * *